Figure 1:
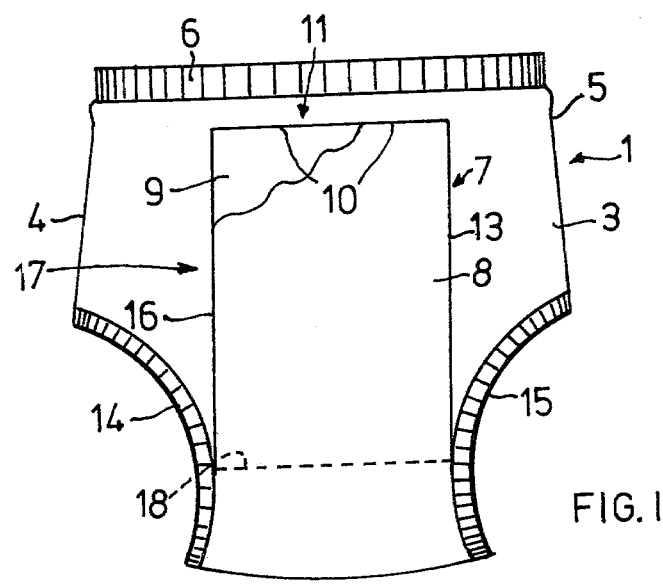

United States Patent [19]

Lowe et al.

[11] 4,326,302
[45] Apr. 27, 1982

[54] UNDERPANTS

[75] Inventors: David R. Lowe, Brinscall; Gerard J. Hay, Chlorley, both of England

[73] Assignee: Courtaulds Limited, London, England

[21] Appl. No.: 65,739

[22] Filed: Aug. 10, 1979

[30] Foreign Application Priority Data

Aug. 25, 1978 [GB] United Kingdom ............... 34702/78

[51] Int. Cl.³ .............................................. A41B 9/02
[52] U.S. Cl. .................................................... 2/405
[58] Field of Search ............... 2/405, 403, 404, 406, 2/22; 128/159

[56] References Cited

U.S. PATENT DOCUMENTS 3,441,022 4/1969 Severson et al. ................. 2/405
4,035,844 7/1977 Atack et al. ........................ 2/22

FOREIGN PATENT DOCUMENTS 165440 9/1954 Australia ................................ 2/406
678623 9/1952 United Kingdom ................. 2/405
1411087 11/1975 United Kingdom ................. 2/406

*Primary Examiner*—H. Hampton Hunter
*Attorney, Agent, or Firm*—Davis, Hoxie, Faithfull & Hapgood

[57] ABSTRACT

Underpants suitable for use by male persons, have a pouch for holding a fluid-absorbing pad, and a fly opening. The latter makes the underpants more acceptable to men and in some cases appears to give psychological help for reducing incontinence. The pouch is preferably external, with an impermeable outer panel to prevent leakage from the pad. The inner panel of the pouch is permeable and made of a hydrophobic fabric such as polyester to keep the wearer dry and comfortable. The fly opening is conveniently located at or adjacent to a side of the pouch at the front of the underpants. It may have a fastening.

3 Claims, 2 Drawing Figures

U.S. Patent    Apr. 27, 1982    4,326,302

UNDERPANTS

This invention relates to underpants having a pouch for holding a pad capable of absorbing body fluids. Underpants of this type are described in our British Patent Specification No. 1,411,087 and are of particular benefit for incontinent persons. They have achieved widespread acceptance for this purpose, both for use domestically and in institutions such as hospitals, but the overwhelming majority of users are women. This does not reflect the statistics of incontinent persons, but is thought to be the result of a psychological aversion by men to wearing what is apparently regarded as a female garment.

According to this invention, underpants suitable for use by male persons have an elongate pouch which is provided with an opening for insertion of a fluid-absorbing pad therein and which extends at least over a region of the underpants which will lie over the genital area in use, and have a fly opening.

The pouch preferably extends up the front of the underpants beyond the region which will cover the genital area so that the risk of the pad being avoided by involuntary discharges of urine is minimised in most circumstances. In the other direction the pouch extends into the crotch region of the underpants and preferably is extended to cover the anal area in use. The fly opening is conveniently located at or adjacent to a side portion of the pouch at the front of the underpants.

In order to make pad changing easier, particularly for geriatric patients, the pouch opening is preferably external of the underpants and preferably located at or adjacent to an end of the pouch at the front of the underpants. It is also preferred that the pouch itself is externally located for a number of reasons. It simplifies manufacture because the pouch can be made separately and then secured to the main body of the underpants later. This is desirable in a preferred construction of pouch having an inner panel of a liquid-permeable material and an outer panel of a liquid impermeable material, because it avoids having to incorporate liquid-impermeable panels in the main body of the underpants, and allows them to be constructed from normal permeable fabric. This fabric, and the liquid-permeable material which comprises the inner panel of the pouch may be hydrophobic fabrics such as polyester fabric which allows urine to pass through to the pad but absorbs minimal amounts itself. In this way, the wearer can stay dry and comfortable.

The liquid-impermeable outer panel of the pouch prevents leakage from the pad. It may comprise a plastics or rubber sheet material preferably in the form of a coated fabric, for example a polyurethane-coated nylon fabric.

External location of the pouch also allows a construction of the fly opening which may be in the conventional form for men's underpants. The pouch simply overlies the front panel of the underpants and does not interfere with the use of the fly opening. For example, the front panel may terminate in a free lower edge in the region which will cover the genital area in use. The pouch may then partially overlie the front panel and be secured to it, and extend over and below the free lower edge of the front panel into the crotch region of the underpants. The fly opening may be formed between the front panel of the underpants and a side portion of the pouch overlying the front panel so as to allow access from outside the underpants to the free lower edge of the front panel. Thus, the pouch may be secured to the front panel by stitching around the pouch margins which overlie the front panel, but leaving it unstitched along at least a portion of one side margin so as to provide the fly opening.

The fly opening may be left unfastened or may be provided with a fastening to reduce the risk of the fly gaping open under the weight of the pad in the pouch.

We find that the fly opening makes the underpants more acceptable to men. In some cases the degree of incontinence of men wearing the underpants has been reduced, and it is believed that this is a consequence of the reduction of the anxiety caused by incontinence, because the underpants give a feeling of safety, coupled with the convenience and masculine nature of the fly opening which promote a desire to use it.

The underpants of the invention may have leg portions, but are preferably without them and in the form of briefs to give a close fit around the leg opening. In other respects, it is desirable that the underpants of the invention should have the features normally associated with men's underpants as distinct from women's. Thus, it is preferred that the waistband be of the usual wide, elasticated form and that the leg openings are elasticated in the usual way for men's underpants with a comparatively wide seam.

Figure 2:
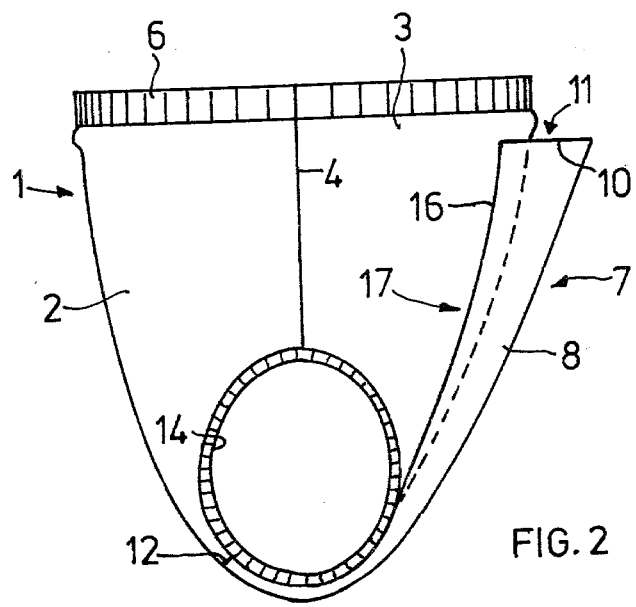

The invention is illustrated by way of example by the accompanying drawing in which:

FIG. 1 is a schematic front view of underpants according to the invention, with part of the pouch broken away to reveal the underlying construction, and FIG. 2 is a schematic side view of the same underpants.

Referring to both Figures of the drawing, the underpants 1 comprise a back panel 2 of fabric sewn to a front panel 3 of fabric along side seams 4 and 5. Both front and back panels extend across the full width of the underpants from side seam to side seam and both are sewn at their upper margins to an elasticated waistband 6.

An elongate pouch 7 partially overlies front panel 2 and extends below front panel 2 into the crotch region of the underpants. Pouch 7 comprises an outer rectangular panel 8 of waterproof fabric (for example a polyurethane-coated nylon fabric) and an inner rectangular panel 9, which may be of a hydrophobic fabric, such as polyester fabric, and may be of the same fabric as the rest of the underpants, for example knitted polyester fabric. The inner panel is the same size as the outer panel and the margins of both panels are sewn together except for the upper margins 10 to provide an enclosed pouch with an upper opening 11 for inserting a fluid-absorbing pad. The pouch 7 is secured externally on the underpants by sewing and is joined to the back panel 2 along rear seam 12 and to the front panel 3 along upper right-hand seam 13 (as viewed in FIG. 1) and along the upper margin 10 of the inner panel 9 only of the pouch.

The back and front panels 2 and 3, respectively, are both shaped at their lower side margins, and define, together with the pouch 7, elasticated leg openings 14 and 15.

The upper left-hand side margin 16 (as viewed in FIG. 1) of the pouch is not sewn to the front panel, so as to provide a fly opening 17 between them. This provides access to the inside of the underpants by way of the lower margin of the front panel which terminates as a free edge 18 in the region of the underpants which will cover the genital area in use. This edge 18 comes sufficiently low down that in normal wearing of the pants the front panel provides the required support.

What is claimed is:

1. Underpants suitable for use by male persons comprising:
   (a) material configured to provide a waist opening and a pair of leg openings including a front panel terminating in a free lower edge in the genital area; and
   (b) an externally located elongate pouch secured to said front panel, comprising an inner panel of a liquid-permeable material and an outer panel of a liquid-impermeable material, and being provided with an opening for insertion of a fluid-absorbing pad, said pouch partially overlying the front panel and extending over and below said free lower edge into the crotch region; and
   (c) a fly opening between the front panel and a side portion of the pouch overlying said front panel, whereby exit for normal micturition is provided under said free lower edge and thence laterally out the fly opening.

2. Underpants as claimed in claim 1 in which the pouch opening is located at or adjacent to an end of the pouch at the front of the underpants.

3. Underpants as claimed in claim 1 in which the liquid permeable material is a hydrophobic fabric.

* * * * *